United States Patent [19]

Gupta

[11] 4,148,889

[45] Apr. 10, 1979

[54] TREATMENT OF VIRAL INFECTIONS

[75] Inventor: Vidya S. Gupta, Saskatoon, Canada

[73] Assignee: Canadian Patents and Development Limited, Ottawa, Canada

[21] Appl. No.: 748,695

[22] Filed: Dec. 8, 1976

[51] Int. Cl.² ............................................ A61K 31/70
[52] U.S. Cl. .................................................. 424/180
[58] Field of Search ........................... 424/180; 536/23

[56] References Cited
PUBLICATIONS

Chemical Abstracts 84: 130156a (May 10, 1976).

Primary Examiner—Jerome D. Goldberg
Attorney, Agent, or Firm—Alan A. Thomson

[57] ABSTRACT

The compound 5-methoxymethyldeoxyuridine has been found to have useful therapeutic properties. Animal tests have shown antiviral activity against herpes simplex viruses, e.g., in treatment of herpes keratitis and herpes encephalitis. An enhanced activity has been observed when administered in conjunction with arabinosyl adenine. Immunostimulant properties have also been observed in vivo.

9 Claims, 3 Drawing Figures

TREATMENT OF VIRAL INFECTIONS

FIELD OF THE INVENTION

This invention is concerned with the therapeutic use of 5-methoxymethyldeoxyuridine (1-(2-deoxy-$\beta$-D-ribofuranosyl)-5-methoxymethyluracil), MMUdR, in animals including man as an antiviral agent or as an immunostimulant or both. This compound MMUdR has shown very significant activity in vivo against certain herpes viruses, particularly herpes simplex (HSV-1). This compound has also been found to stimulate the immune system as described more fully below.

DESCRIPTION OF THE PRIOR ART

In the search for effective drugs for the treatment of herpes viruses, considerable interest has been shown in the use of nucleoside analogues. Previously, 5-iodo-2'-deoxyuridine (IUdR), cytosine arabinoside (Ara-C), and arabinofuranosyladenine (Ara-A) have been found to be effective in varying degrees in the treatment of infections due to herpes viruses. However, their high toxicity (especially to rapidly proliferating cells), limits the usefulness of these nucleoside analogues in the treatment of viral infections.

Recently 5-methoxymethyldeoxyuridine (MMUdR) has been synthesized and some inhibitory activity observed in monolayer cultures of secondary bovine fetal kidney cells against the cytopathogenic effects of bovine rhinotracheitis virus. This MMUdR compound is a white powder of m.p. 120°–125° C. having the formula:

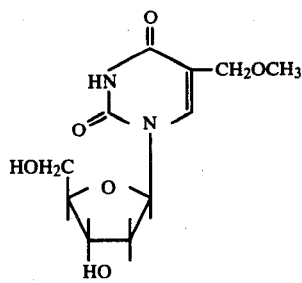

SUMMARY OF THE INVENTION

Animal tests have now shown that MMUdR is active in vivo against certain herpes viruses, particularly herpes simplex (HSV-1). For example, significant activity in vivo has been demonstrated against herpes keratitis and herpes encephalitis. Animal tests have shown a synergistic activity against HSV-1 induced keratitis infection, when MMUdR was used in conjunction with arabinosyl adenine (Ara-A). No significant toxicity was observed even at high doses and MMUdR appears to be devoid of teratogenic activity.

Animal tests also revealed an immunostimulant activity for MMUdR particularly at doses above about 500 mg/kg body weight.

A much lower antiviral activity for MMUdR was observed against the following viruses in cell cultures: equine rhinopneumonitis virus, murine cytomegalovirus, feline rhinopneumonitis virus and vaccinia virus.

DESCRIPTION OF DRAWINGS

In the accompanying drawings

DETAILED DESCRIPTION AND PREFERRED EMBODIMENTS

Figure 1:
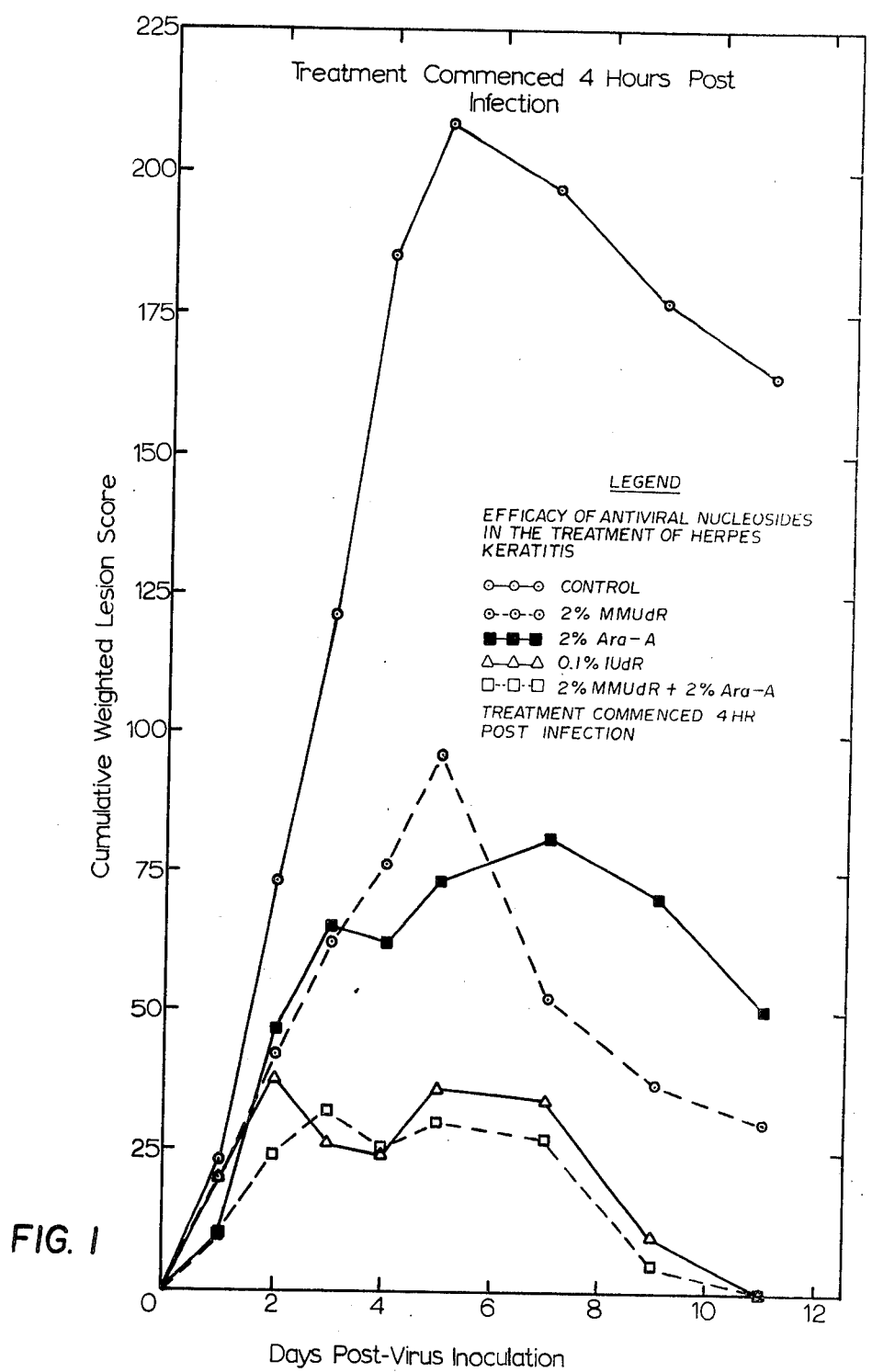
FIG. 1 is a graph of the cumulative weighted lesion score vs. time in days after inoculating with virus (infection) for different treating agents, with treatment commencing four hours post infection.

The MMUdR compound can be administered parenterally or topically for therapeutic use, e.g., intraperitoneally, intravenously, intramuscularly, subcutaneously, etc. The compound may be dissolved or dispersed in any physiologically-acceptable liquid carrier, e.g., physiological saline, or in any suitable ointment base for topical application. MMUdR is water-soluble, and aqueous solutions of from about 1 to about 10% concentration are conveniently used. For treatment of Herpes Keratitis (eye infection), a solution of 2–5% singlely and 1–2% in combination with 1–2% Ara-A has been found to be very effective. The dosage of MMUdR can be any effective (antiviral or immunostimulant) amount up to about 2000 mg/kg of body weight or more. A dose of 4000 mg/kg is the maximum dose administered and no mortality was observed in test animals after administration of this single dose. No morbidity or loss in weight was observed in animals even after administration of massive cumulative amounts of 15 g/kg total dosage. A preferred parenteral dosage range for treatment of systemic viral infections is from about 500 to about 2000 mg/kg. A preferred parenteral dosage range for immunostimulant purposes is from about 500 to about 2000 mg/kg. These dosages can be repeated at suitable intervals, e.g., daily, or more often if desired, until the desired effect is attained.

An enhanced activity against herpes simplex virus has been observed when MMUdR is administered in conjunction with arabinosyl adenine (Ara-A). When this combined treatment is used, the relative proportions may vary widely but are usually within about 50 to about 200% by weight of MMUdR based on the Ara-A. The preferred antiviral dosage range for the combination is similar to that given above for MMUdR alone.

The Ara-A (9-$\beta$-D-arabinofuranosyl adenine) has the formula:

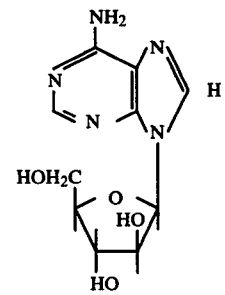

This compound can also be administered by the same routes and in the same carriers as for the MMUdR. It is preferred to administer a mixture of the two compounds.

The following Examples are illustrative.

EXAMPLE 1

TREATMENT OF HERPES SIMPLEX (HSV-1) KERATITIS

Comparative efficacy of MMUdR, IUdR and Ara-A in the treatment of HSV-1 induced keratitis in rabbit eye has been determined. Rabbits weighing 2-3 kg were used in these experiments. The eyes of each rabbit were anesthetized by instilling a couple of drops of ophthalmic proparicane (local anaesthetic 0.5% solution). The cornea was scarified (using 26 gauge needle) by making three vertical and three horizontal scratches on the surface of the cornea. The degree and uniformity of scarification in each case was checked under u.v. light after fluorescein staining. One eye (left) of each rabbit was infected with 0.1 ml (1000 PFU plaque-forming units) of HSV-1 by instilling the virus solution. The right eye was used as a toxicity control (to determine the effect of the drug on corneal wound healing). Treatment was initiated four hours after infection. Eye drops (1-2) were placed in both eyes hourly or every two hours during the day (8 A.M.-6 P.M.) for 10 days. MMUdR, was dissolved in 1% polyvinyl alcohol and tried at different concentrations (0.1-10%) and compared with ophthalmic solution of IUdR (Herplex (trademark) 0.1%) and Ara-A suspension (5%). MMUdR and Ara-A were effective at concentrations ≧2% in contrast to IUdR which was effective at 0.1%. Total days of treatment required were 8 to 10 days for complete eradication of infection. These results indicate that MMUdR was as potent as Ara-A. No corneal toxicity was observed with MMUdR at concentrations up to 10%.

Thus, MMUdR is effective in the treatment of herpes keratitis in animal tests. IUdR (0.1%) ophthalmic solution has been shown to be "teratogenic" in rabbits. Therefore, even though MMUdR is less active than IUdR, because it is essentially devoid of mammalian toxicity, its use may be preferable in the treatment of herpes keratitis infections in humans.

EXAMPLE 2

TREATMENT OF HERPES SIMPLEX (HSV-1) KERATITIS

Test Solutions:

(i) MMUdR was dissolved in sterile physiological saline (0.85%). This solution was added to Adsorbotear (Trademark for an artificial tear solution), to give a final concentration of 20 mg/ml (2%) or 50 mg/ml (5%).

(ii) Ara-A (arabinosyl adenine) was suspended in Adsorbotear to give a final concentration of 20 mg/ml (2%) or 50 mg/ml (5%). In this vehicle Ara-A remains fairly suspended. However, prior to use, the container was shaken to ensure that a homogeneous suspension was used in eye.

(iii) IUdR (Herplex, 0.1%) was used as supplied.

Figure 2:
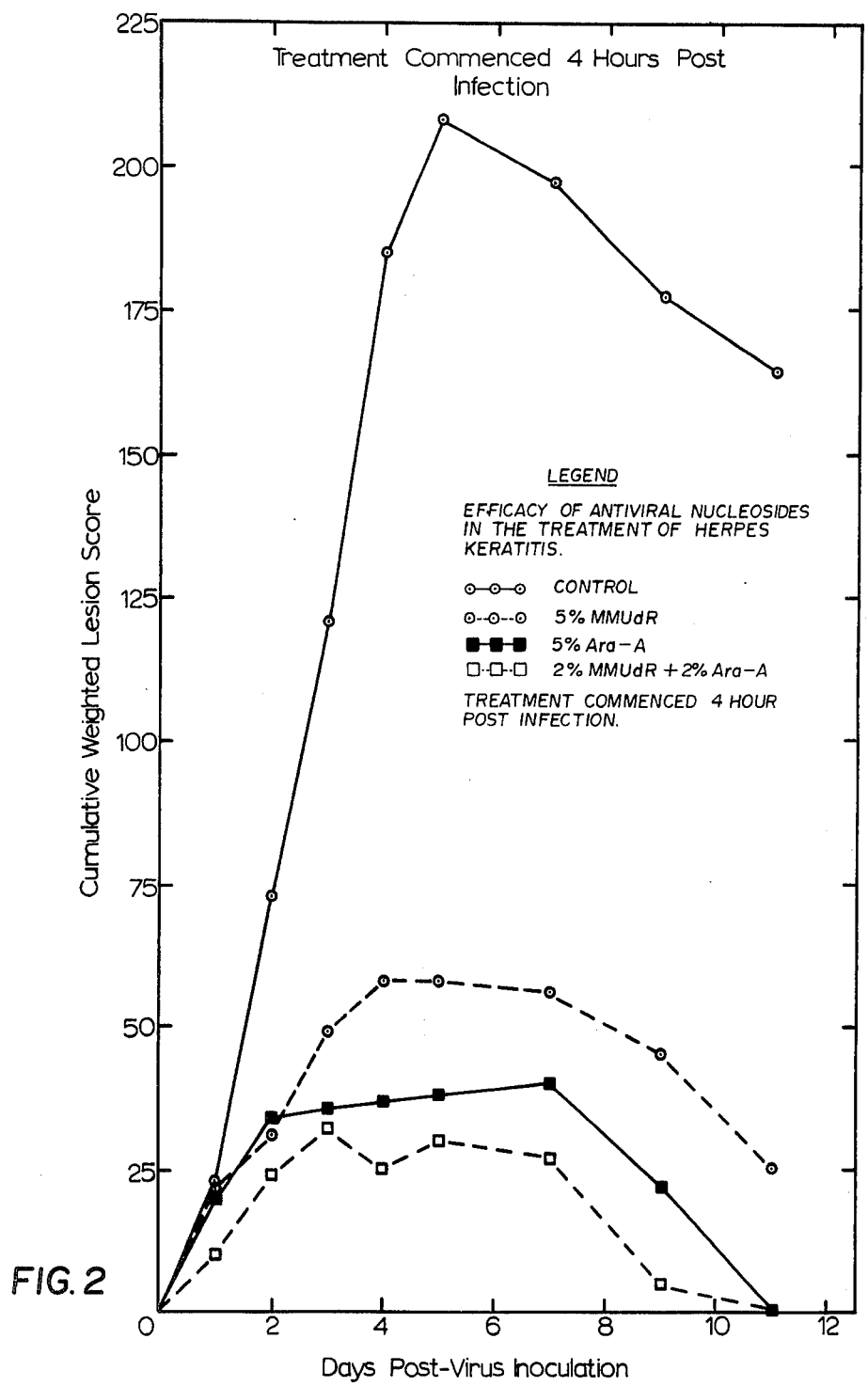
FIG. 2 is similar to FIG. 1 with increased concentration of treating agents.
Figure 3:
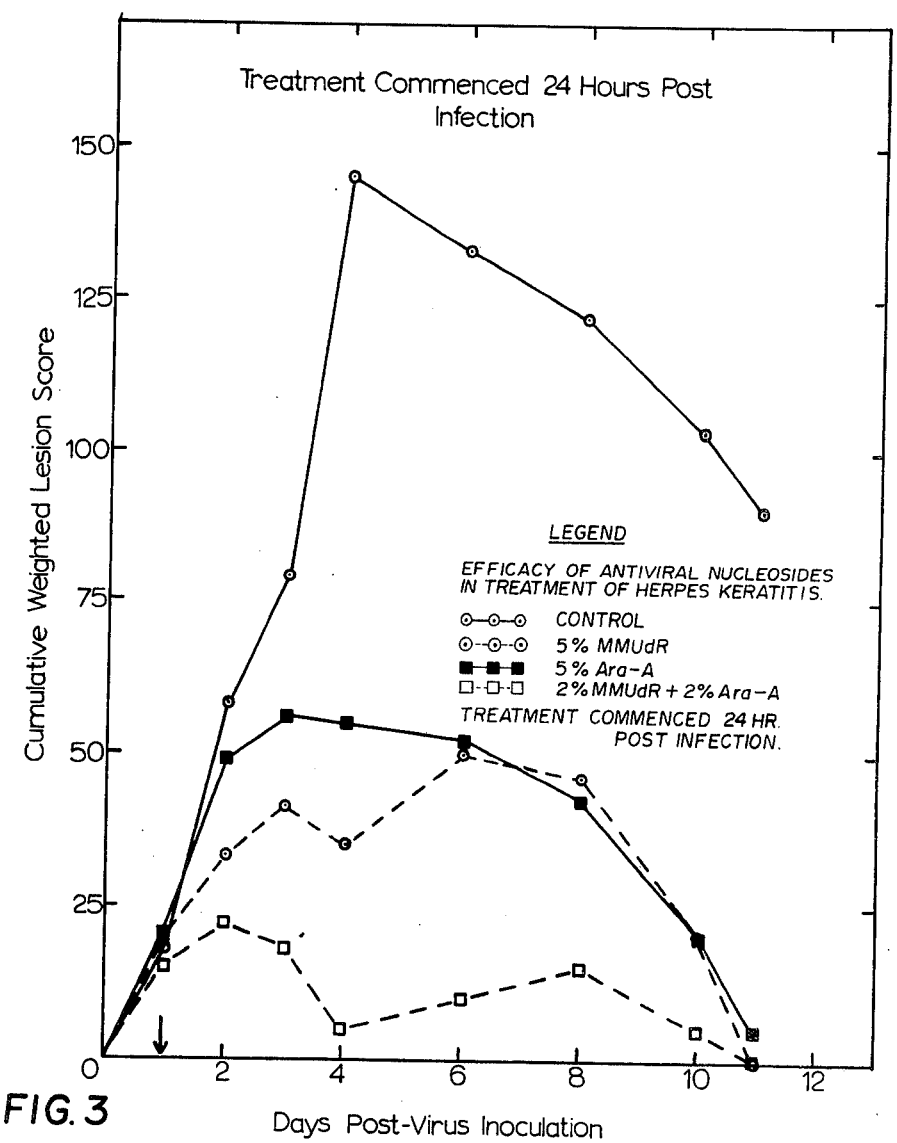
FIG. 3 is similar to FIG. 2 with the treatment commencing 24 hours after infection.

The comparative efficacy of MMUdR, IUdR, Ara-A and combination of MMUdR+Ara-A in the treatment of HSV-1 induced keratitis (deep stromal lesions) in rabbit eye was determined in further tests. Treatment was initiated either four or twenty four hours after infection. On alternate days, each eye was examined, both grossly and after fluorescein staining for grading the severity of ocular lesions. The method of Crown et al, (investigative ophthal, 2, 578 (1963)) as modified by Sidwell et al (Antimicro. Agents and Chemo. 3, 242 (1973)) for grading severity of ocular lesions, was used. The parameters measured were: infectivity (lesion size and type, corneal opacity) and Draize response (erythema, chemosis, discharge) on a weighted grading scale. (i) infectivity reading: scores of 0 (uninfected) to 4 (maximal severity); daily accumulation (infectivity scores×10); (ii) Draize parameters: similar scores - 0 (uninfected) to 4 (maximal severity). The combined weighted infectivity and Draize scores of the control and drug-treated eyes were then plotted together and compared. The results of these experiments (i.e. cumulative weighted score and days post virus inoculation) are summarized in FIGS. 1-3.

CONCLUSIONS:

(i) MMUdR at 2% and 5% concentration was found to have potent anti-keratitis activity in rabbit eye. On weight basis, it appears to be as potent as Ara-A.

(ii) MMUdR in combination with Ara-A showed synergistic effect against HSV-1-induced keratitis infection.

(iii) Antiherpes activity was seen by all scoring parameters tested.

(iv) MMUdR was effective in inhibiting the inflammatory (Draize) reaction to HSV-1 virus.

(v) It was also effective in preventing the development of virus-induced lesions as determined by scoring of opacity and by microscopic examination of fluorescein stained corneas.

(vi) No corneal toxicity was observed with up to 10% concentration of MMUdR.

EXAMPLE 3

TREATMENT OF HERPES ENCEPHALITIS (HSV-1) INFECTIONS IN MICE

Swiss mice (15 g) were inoculated intracerebrally with 50 pfu of HSV-1 virus (this virus dose has been found to produce 80–90% mortality between 5th and 10th days post infection). A single dose of MMUdR (in saline solution) was administered at 500, 1,000, 1,500 and 2,000 mg/Kg/day, i.p. for 5 days. Treatment was initiated 6 hours post inoculation of virus. Antiviral activity was assessed: (i) by increase in mean survival time and (ii) survivors among the treated infected mice. The animals were observed for 21 days, and deaths occurring were recorded daily. The results are summarized in Table I.

TABLE I

Efficacy of MMUdR in the Treatment of Herpes Simplex Virus[a] Enchephalitis-Induced Deaths in Mice.

| Treatment | Virus Controls | MMUdR (1500 mg/Kg)[b] | MMUdR (2000 mg/Kg)[b] |
|---|---|---|---|
| Survivors | 3/10 | 7/10 | 9/10 |
| Mean Survival Time | 238 | 395 | 455[c] |

[a]50 pfu/mouse - intracerebrally; 15 gm Swiss mice.
[b]intraperitoneal daily for 5 days, treatment was initiated 6 hours post virus inoculation.
[c]statistically significant P <0.05.

CONCLUSIONS:

(i) MMUdR at a dose of 1500 mg/Kg gave marked increase in life span (355 hr.) as compared to control mice (238 hr.) and also increased number of survivors.

(ii) MMUdR at 2,000 mg/Kg/day gave complete protection of HSV-1 infected mice. One death observed was due to secondary infection.

EXAMPLE 4

IMMUNE RESPONSE STUDIES (IN VIVO)

To assess the effects of MMUdR on immune responsiveness, three antigens were studied - HSV-1, *Brucella abortus* (killed) and sheep erythrocytes (SRBC). Groups of (BALB/C×C3H) Fl mice 8–10 weeks of age weighing between 20–21 g were injected twice daily with varying doses (20–2,000 mg/Kg) of MMUdR. The first daily injection was given intravenously (i.v.) and the second 8 hours later, intraperitoneally (i.p.). Drug treatments were continued for 9 days. To assess the effects of drug administration on immune responsiveness, 4 days after daily treatment, animals were injected with one of the following antigens - 0.2 ml of 25% washed SRBC given i.v.; $10^{10}$ killed *Brucella abortus* organisms given i.p. or $10^8$ plaque forming units (pfu) equivalents of ultraviolet irradiated HSV-1 given simultaneously. Mice receiving HSV-1 antigen had been primed 6 weeks before by infection with HSV-1. Drug treatments were continued for 5 days after antigen administrations. The results of these experiments are summarized in Tables II and III. It is apparent that immunosuppression was not induced even at the highest levels of drug administration tested (2,000 mg/Kg). On the contrary, in both experiments, the numbers of antibody forming cells (AFC) were higher in the groups that received the highest levels of drug than in the control group (Table II).

Drug administration also had no immunosuppressive effects against antibody responses to HSV-1 or to *Brucella abortus* (Table III). In addition, the data included in Table II also clearly shows that MMUdR was well tolerated by mice at least for the 9 day treatment period.

(ii) There was evidence of stimulation of immune response after administration of MMUdR at the doses i.v., 1,000 mg/Kg; i.p., 2,000 mg/Kg.

EFFECT OF MMUdR ON IMMUNE RESPONSE (IN VITRO)

Recovery from herpes virus infection possibly depends upon an intact lymphoid system. Therefore, tests were undertaken to study the effects of MMUdR on lymphoid functions. MMUdR did not have any immunosuppressive effects on lymphoid functions. In contrast, in two preliminary trials, it was found to have immunostimulant activity. This property is highly desirable for eradication of virus infections. MMUdR should be useful in counteracting the immunosuppressive properties of other drugs.

EXAMPLE 5

TERAOGENIC STUDY

Fifteen bred female mice (Swiss) were injected intraperitoneally once daily with 500 mg/Kg of MMUdR. Treatment was commenced on the day of initiation of breeding (as evidenced by sperm in vagina) and continued throughout gestation period (21 days). Altogether, approximately 10 gm/Kg of MMUdR was received by each pregnant female mouse. Control mice were given an equivalent amount of saline.

No drug effects were observed

The young of the dosed and control groups showed comparable livability and body weight gains during the five-week nursing period. At weaning, physical examination and necropsy revealed no drug-related morphological abnormalities.

Effect on the mouse fetus:

On day 19 after initiation of treatment; fetuses from

TABLE II

| | | | Effect of MMUdR on Antibody Forming Cell Response to Sheep Erythrocytes | | | |
|---|---|---|---|---|---|---|
| | Dose MMUdR | Route of | Mean ± SD | Mean ± SD number | Mean ± SD Body Weight | |
| Experiment | (mg)[1] | Injection | AFC[2]/spleen | of cells per spleen | Initial[3] | Final |
| A | 20 (1000) | i.v. | 17165±2280 | 148±24 | 20.1±1.7 | 20.4±1.0 |
| A | 2 (100) | i.v. | 15387±4962 | 171±23 | 21.4±1.4 | 20.6±1.8 |
| A | 0 | — | 15280±5867 | 187±19 | 20.0±2.0 | 20.3±1.3 |
| B | 40 (2000) | i.p. | 42750±10816 | 211±16 | ND[4] | ND |
| B | 4 (200) | i.p. | 28950±8433 | 245±32 | ND | ND |
| B | 0.4 (20) | i.p. | 32350±5307 | 200±42 | ND | ND |
| B | 0 | — | 39045±9300 | 215±24 | ND | ND |

[1]All drug administrations were divided into equal aliquots and given twice daily. The dose shown equal the total dose per day. The values in brackets equals the approximate dose in mg/Kg using an assumed body weight of 20g for computation.
[2]Antibody forming cells determined by the method of Cunningham and Szenberg (Ref: Cunningham A and A. Szenberg Immunology 14, 599 (1968)).
[3]Expressed in grams.
[4]Not done.

TABLE III

| Mean Log₂ Antibody Titers of Mice Immunized with Herpes Simplex Type I and Brucella Abortus | | |
|---|---|---|
| | Mean ± SD Antibody Titer | |
| Group | HSV-1 | Brucella |
| Drug treated[1] | 4.75±0.4 | 4.5±0.7 |
| Controls | 4.5±0.8 | 5.0±1.1 |

[1]Animals were treated with 2000 mg/kg daily (divided into 2 equal doses) for 4 days, immunized with 10[10] killed Brucella abortus organisms and with 10[8] pfu equivalents of UV-inactivated HSV-1. These mice had been infected with HSV-1 6 weeks previously. Drug administration was continued for a total of 9 days and serums were collected at 10 days after immunization for antibody titrations.

CONCLUSIONS:

(i) MMUdR failed to show immunosuppressive activity up to doses as high as 2,000 mg/Kg given daily for 9 days.

six treated (MMUdR, 500 mg/Kg, i.p. for 18 days) and six control (saline, i.p. for 18 days) mice were removed by caesarian and checked for pathology of reproductive tract of dam, resorption sites, litter size, weight, sex-ratio and any gross abnormalities. No differences were apparent between control and treated groups.

CONCLUSION:

MMUdR appears to be devoid of teratogenic activity in mice.

SUMMARY OF ANIMAL EXPERIMENTS (i) MMUdR was extremely well tolerated after intraperitoneal (i.p.) administration in mice.

$LD_0 = 4000$ mg/Kg (maximum single dose administered)

$LD_0 = 2000$ mg/Kg/day for 10 days (ii) Clinical Chemistry and hemogram data of treated animals were normal.

(iii) MMUdR was found to have potent anti-keratitis activity in the rabbit eye.

(iv) In combination with Ara-A, MMUdR showed synergistic activity against HSV-1 induced keratitis infection.

(v) MMUdR was effective in providing protection against HSV-1 induced encephalitis infection in mice.

(vi) MMUdR appeared to be devoid of teratogenic activity in mice even after administration of massive doses of drug (500 mg/Kg/day, i.p.) for the entire gestation period (20 days).

(vii) MMUdR failed to elicit immunosuppressant activity in mice. Animals treated with doses as high as 2000 mg/Kg/day for 9 days produced normal immune responses to sheep erythrocytes, Brucella bacteria and Herpes Simplex virus. Lymphoid functions appeared normal.

(viii) MMUdR showed stimulation of immune response at the higher doses.

Ophthalmic ointments of MMUdR can be prepared using white petrolatum-mineral oil base (optionally containing anhydrous lanolin) or polyethylene-gelled mineral oil base. Preferably, concentrations in the range of about 5 to 15% for MMUdR are used. Principal advantages of these preparations are: (i) prolonged contact and effect, (ii) lack of irritation on initial instillation, and (iii) greater storage stability.

I claim:

1. A method of treating infections of herpes simplex viruses in animals comprising
   administering 5-methoxymethyldeoxyuridine parenterally or topically to said animal an amount effective to alleviate the symptoms of said viral infection.

2. The method of claim 1 wherein the parenteral dosage is within about 2 to about 3000 mg/kg body weight.

3. The method of claim 1 wherein the compound is injected dissolved in an aqueous liquid medium.

4. The method of claim 1 wherein the compound is applied topically in solution of ointment form.

5. The method of claim 1 wherein the 5-methoxymethyldeoxyuridine (a) is administered in conjunction with arabinosyl adenine (b), the proportions of (a) being within about 50 to about 200% based on the wt. of (b).

6. The method of claim 5 wherein the proportions of (a) and (b) are approximately equal.

7. A pharmaceutical composition comprising
   (a) 5-methoxymethyldeoxyuridine and
   (b) arabinosyl adenine, the proportions of (a) being within about 50 to about 200% based on the wt. of (b).

8. The composition of claim 7 wherein the proportions of (a) and (b) are approximately equal.

9. The composition of claim 7 including a physiologically-acceptable liquid carrier or an ointment base.

* * * * *